(12) United States Patent
Kotilahti et al.

(10) Patent No.: US 12,611,123 B2
(45) Date of Patent: Apr. 28, 2026

(54) MYOCARDIAL SPECTROMETER PROBE AND A METHOD OF MONITORING THE HEART MUSCLE

(71) Applicant: SPECTROCOR OY, Espoo (FI)

(72) Inventors: Kalle Kotilahti, Espoo (FI); Tommi Pätilä, Espoo (FI)

(73) Assignee: SpectorCor Oy, Espoo (FI)

( * ) Notice: Subject to any disclaimer, the term of this patent is extended or adjusted under 35 U.S.C. 154(b) by 767 days.

(21) Appl. No.: 17/797,163

(22) PCT Filed: Feb. 3, 2021

(86) PCT No.: PCT/FI2021/050074
§ 371 (c)(1),
(2) Date: Aug. 3, 2022

(87) PCT Pub. No.: WO2021/156544
PCT Pub. Date: Aug. 12, 2021

(65) Prior Publication Data
US 2023/0046929 A1 Feb. 16, 2023

(30) Foreign Application Priority Data
Feb. 3, 2020 (FI) ..................................... 20205108

(51) Int. Cl.
| | |
|---|---|
| *A61B 5/1455* | (2006.01) |
| *A61B 5/00* | (2006.01) |
| *A61B 5/01* | (2006.01) |
| *A61B 5/1459* | (2006.01) |
| *A61B 90/00* | (2016.01) |
| *A61N 1/05* | (2006.01) |

(52) U.S. Cl.
CPC ............ *A61B 5/14552* (2013.01); *A61B 5/01* (2013.01); *A61B 5/1459* (2013.01); *A61B 5/6852* (2013.01); *A61B 2090/034* (2016.02); *A61B 2560/0223* (2013.01); *A61B 2562/0233* (2013.01); *A61B 2562/16* (2013.01); *A61B 2562/185* (2013.01); *A61N 1/0595* (2013.01)

(58) Field of Classification Search
CPC ..... A61B 5/1455; A61B 5/14552; A61B 5/01; A61B 5/1459
See application file for complete search history.

(56) References Cited

U.S. PATENT DOCUMENTS

| | | |
|---|---|---|
| 5,161,531 A | 11/1992 | Parsons et al. |
| 5,865,738 A | 2/1999 | Morcos et al. |
| 6,564,088 B1 | 5/2003 | Soller et al. |
| (Continued) | | |

FOREIGN PATENT DOCUMENTS

| | | |
|---|---|---|
| CN | 1745294 A | 3/2006 |
| CN | 1022920199 A | 12/2011 |
| (Continued) | | |

*Primary Examiner* — Marjan Fardanesh
(74) *Attorney, Agent, or Firm* — Laine IP Oy

(57) ABSTRACT

The present invention relates to a myocardial spectrometer probe, comprising: at least two separate light guides (120A, 120B), insertable in a tissue, wherein a first light guide (120A, 120B) is arranged to deliver light and a second light guide (120A, 120B) is arranged to collect light, and wherein the first light guide (120A, 120B) and the second light guide (120A, 120B) are arranged distinct to each other.

25 Claims, 5 Drawing Sheets

(56)                         References Cited

U.S. PATENT DOCUMENTS

| | | | |
|---|---|---|---|
| 10,064,554 B2 * | 9/2018 | Floyd .................... A61B 5/0075 |
| 2001/0012429 A1 | 8/2001 | Wach et al. |
| 2006/0241364 A1 | 10/2006 | Ince |
| 2007/0051379 A1 | 3/2007 | Lash et al. |
| 2008/0125634 A1 | 5/2008 | Ryan et al. |
| 2009/0075321 A1 | 3/2009 | Obeid et al. |
| 2011/0112435 A1 | 5/2011 | Ramanujam et al. |
| 2013/0295192 A1 | 11/2013 | Hirsch et al. |
| 2014/0200421 A1 | 7/2014 | Gilland |
| 2014/0343384 A1 | 11/2014 | Floyd et al. |

FOREIGN PATENT DOCUMENTS

| | | | |
|---|---|---|---|
| CN | 105434041 A | 3/2016 |
| CN | 104066368 B | 2/2017 |
| EP | 3175780 A1 | 6/2017 |
| JP | S58185170 A | 10/1983 |
| JP | H05115465 A | 5/1993 |
| JP | H0716299 A | 1/1995 |
| JP | H11502748 | 3/1999 |
| JP | 3474662 B2 | 12/2003 |
| JP | 2006518631 A | 8/2006 |
| JP | 2007204398 A | 8/2007 |
| JP | 2007526021 A | 9/2007 |
| JP | 2010029564 A | 2/2010 |
| JP | 2015081916 A | 4/2015 |
| WO | WO9519135 A1 | 7/1995 |
| WO | WO2004016155 A2 | 2/2004 |
| WO | WO2011091439 A2 | 7/2011 |
| WO | WO2017044941 A1 | 3/2017 |

* cited by examiner

MYOCARDIAL SPECTROMETER PROBE AND A METHOD OF MONITORING THE HEART MUSCLE

TECHNICAL FIELD

The invention concerns in general the field of medical technology. More particularly, the invention concerns a solution for monitoring heart muscle.

BACKGROUND

Open-heart surgery is when a chest is cut open and the surgery is performed on the great veins or arteries establishing an inflow and outflow of the blood to the heart, respectively, or the heart itself, valves, arteries, shunts, muscular obstructions or other disturbances affecting normal function of the heart. In most cases, the heart's pumping action must be stopped in order to be able to perform the operation. When the heart is stopped, coronary blood flow to the myocardium must be blocked. This causes inevitable ischemia to heart. Currently, there are no means to measure heart oxygen availability and metabolism during aortic clamping. Instead, experience and general knowledge of the previous practice is used. Many times, this is enough, but not always. About 20% of the hearts are dysfunctional after the operation due to the perioperative ischemia. This dysfunction is caused by myocardial stunning, which is a reversible reduction of function of heart contraction after reperfusion, not accounted for by tissue damage or reduced blood flow, or by myocardial infarction. But it can also be due to the irreversible myocardial damage due to ischemia.

When operating coronary arteries of the heart, the procedure can also be performed while the heart is beating, i.e. without the help of the heart-lung bypass machine circuit. This is called off-pump surgery. In this procedure, the heart is dislocated for proper establishment of the operation field. Also, in these cases, the heart suffers from ischemia. Due to the dislocation of the heart, the ECG measurement can't reliably detect myocardial ischemia until the heart is repositioned. Currently there are no direct, reliable method to measure the heart oxygenation in order to monitor heart ischemia during distal anastomosis suturing in off-pump surgery.

Almost all oxygen in heart is consumed in the mitochondria by an enzyme called cytochrome-c-oxidase. This is the last enzyme in the electron transport chain which drives ATP production, the final fuel used by the cells. The cells need carrier molecules to deliver the oxygen to cytochrome-c-oxidase. The carrier molecule in the blood is hemoglobin, which brings the oxygen from distance to the cells, and eventually releases the oxygen in tissues where the oxygen partial pressure is low. Within the cell, myoglobin acts as a carrier to bring the oxygen across the cell to mitochondria.

A reliable real-time measurement of heart's oxygen availability and/or metabolic state would enable the operation theatre personnel to perform different maneuvers during operation to improve the heart oxygen supply, reduce oxygen metabolism and eventually reduce the total ischemic load of the heart. Measurement of oxygen delivery by hemoglobin and myoglobin, as well as cytochrome-c-oxidase would give the possibility to improve the safety of heart operations, and treatment of heart patients in general and save the costs of the treatment.

When assessing the oxygenation status of the heart, also measuring reduction state and oxygen concentrations of several other proteins with heme prosthetic groups, such as hemoglobin, myoglobin and other hemoproteins could be obviously beneficial. Also, the ability to measure other molecular concentrations within the oxidative phosphorylation chain within the mitochondria would be beneficial, including but not restricted to cytochromes A, B and C could be incremental in analyzing myocardial metabolism, where the reduction state of the enzymes is important. In many cases, mitochondria show very early damage when cellular stress is happening, and enzyme concentrations responding to mitochondrial stress are of interest. Because the mitochondria produce large amounts of reactive oxygen species (ROS), enzymes involved in catalyzing ROS are of interest as well, such as catalase, superoxide dismutase and peroxidases.

The measurement of the molecular concentrations in the heart muscle is important both during the surgery but also after the surgery. During the intensive care after the surgery, the patient many times suffer for the lowest period of left ventricular function. For example, in a document US 2015/0282747 A1 it is disclosed an oxidation measurement system wherein the measurement is performed by inserting a catheter device in contact with a tissue wall of a subject. At least one drawback of the disclosed solution is that the transcatheter measurement through a tissue wall is not that accurate nor specific.

Hence, there is need to develop further solutions applicable at least in open-heart surgery for monitoring molecular concentrations accurately in a heart muscle during and possibly continue the monitoring after the open-heart surgery. But, also, the monitoring of the heart molecular concentrations would be beneficial during any treatments, where cardiac monitoring could bring additional knowledge for the patient treating personnel.

SUMMARY

The following presents a simplified summary in order to provide basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

It is an object of the invention to provide a medical device for monitoring a tissue.

It is another object of the invention to a medical device which can be use at least in part to provide information on molecular concentrations and/or their oxygenation/oxidation ratios in the tissue.

It is still an object of the invention to provide a method of monitoring a tissue.

The objects of the invention are reached by an apparatus and a method as defined by the respective independent claims.

According to a first aspect, a myocardial spectrometer probe is provided, the myocardial spectrometer comprising: at least two separate light guides, insertable in a tissue, wherein a first light guide is arranged to deliver light and a second light guide is arranged to collect light, and wherein the first light guide and the second light guide are arranged distinct to each other at least in part.

The first light guide and the second light guide may be arranged distinct to each other such that, once they are inserted into the tissue of interest, at least a portion of intact tissue separates the first light guide from the second light guide.

The first light guide and the second light guide may be arranged distinct to each other by mounting the first light guide and the second light guide in a jig.

A tip of the light guide may be angled in 45-90 degrees with respect to a longitudinal axis of the light guide, preferable in 70-90 degrees.

The first light guide and the second light guide may be implemented with one of: as a single optical fiber, optical fiber bundles, a light tube.

For example, at least a portion of at least one of the light guides insertable to the tissue may be coated with a steel tubing.

The myocardial spectrometer probe may further comprise pacing leads arranged to travel along at least one of the light guides. A pacing lead may be electrically connected to the steel tubing coating the at least portion of the at least one of the light guides.

For example, a first pacing lead may be electrically connected to the steel tubing of the first light guide and a second pacing lead may be electrically connected to the steel tubing of the second light guide so as to form a bipolar pacing arrangement comprising an anode and a cathode. Still further, the myocardial spectrometer probe may further comprise a stopper device for adjusting at least one of: an insertion depth of at least one of the light guides in the tissue; an insertion angle of at least one of the light guides in the tissue. The stopper device may e.g., comprise a receiving section for receiving at least the light guides and a light cover section for preventing ambient light to enter the tissue at least in part. The receiving section and the light cover section of the stopper device may be mounted together removably. For example, a fixing wire may be arranged to travel through the stopper device, an end of the fixing wire is arranged to be fixed to the tissue for enabling a tensioning of the light guides with a fixing location of the fixing wire. The fixing wire may be the pacing lead. The fixing may be arranged with one of: an inflatable balloon device, a fixing arrangement arranged with a second wire forming an anchor for the fixing wire, an anchor device.

Furthermore, the myocardial spectrometer probe may further comprise an insertion aid device for penetrating a surface of the tissue for inserting the light guides in the tissue. The insertion aid device may comprise at least one tubular member inside which the light guide is arranged. The light guide may be arranged slidably with respect to the tubular member of the insertion aid device. The insertion aid device may also be arranged to operate as an electrode for the pacing lead coupled to the insertion aid device. An end of the tubular member of the insertion aid device facing the tissue may be sharp in shape. The insertion aid device may be made of one of the following: stainless steel, ceramics, composite material.

Moreover, at least one of: the light cover portion, an inflatable balloon device, a fixing device, a fixing wire may be made of biodegradable material.

The myocardial spectrometer probe may further comprise means for providing measurement data representing a temperature of the tissue.

The myocardial spectrometer probe may further comprise a removably mountable protection cover to protect the first light guide and the second light guide.

The protection cover may be arranged to operate as a calibration target for calibrating a measurement system applying the myocardial spectrometer probe.

The myocardial spectrometer probe can be used for monitoring, for example, molecular concentrations in tissue in real-time e.g., during and after an open-heart surgery.

A method of monitoring molecular concentrations in a tissue of interest by spectroscopy, comprises typically the steps of providing at least two separate light guides, insertable into the tissue, wherein a first light guide is arranged to deliver light and a second light guide is arranged to collect light, inserting the light guides into the tissue of interest such that at least a portion of intact tissue separates the first light guide from the second light guide, so that light delivered by the first light guide will travel through said intact tissue to reach the second light guide.

repeatedly delivering light from the first light guide and collecting light delivered from the first light guide by the second light guide, to form a plurality of signals corresponding to the light collected; and monitoring the signals thus obtained.

The expression "a number of" refers herein to any positive integer starting from one, e.g., to one, two, or three.

The expression "a plurality of" refers herein to any positive integer starting from two, e.g., to two, three, or four.

Various exemplifying and non-limiting embodiments of the invention both as to constructions and to methods of operation, together with additional objects and advantages thereof, will be best understood from the following description of specific exemplifying and non-limiting embodiments when read in connection with the accompanying drawings.

The verbs "to comprise" and "to include" are used in this document as open limitations that neither exclude nor require the existence of unrecited features. The features recited in dependent claims are mutually freely combinable unless otherwise explicitly stated. Furthermore, it is to be understood that the use of "a" or "an", i.e. a singular form, throughout this document does not exclude a plurality.

BRIEF DESCRIPTION OF THE DRAWINGS

Embodiments are illustrated by way of example, and not by way of limitation, in the figures of the accompanying drawings.

FIG. 1 illustrates schematically a monitoring system in which the present invention is applied to.

DESCRIPTION OF THE EXEMPLIFYING EMBODIMENTS

The specific examples provided in the description given below should not be construed as limiting the scope and/or the applicability of the appended claims. Lists and groups of examples provided in the description given below are not exhaustive unless otherwise explicitly stated.

Figure 1:
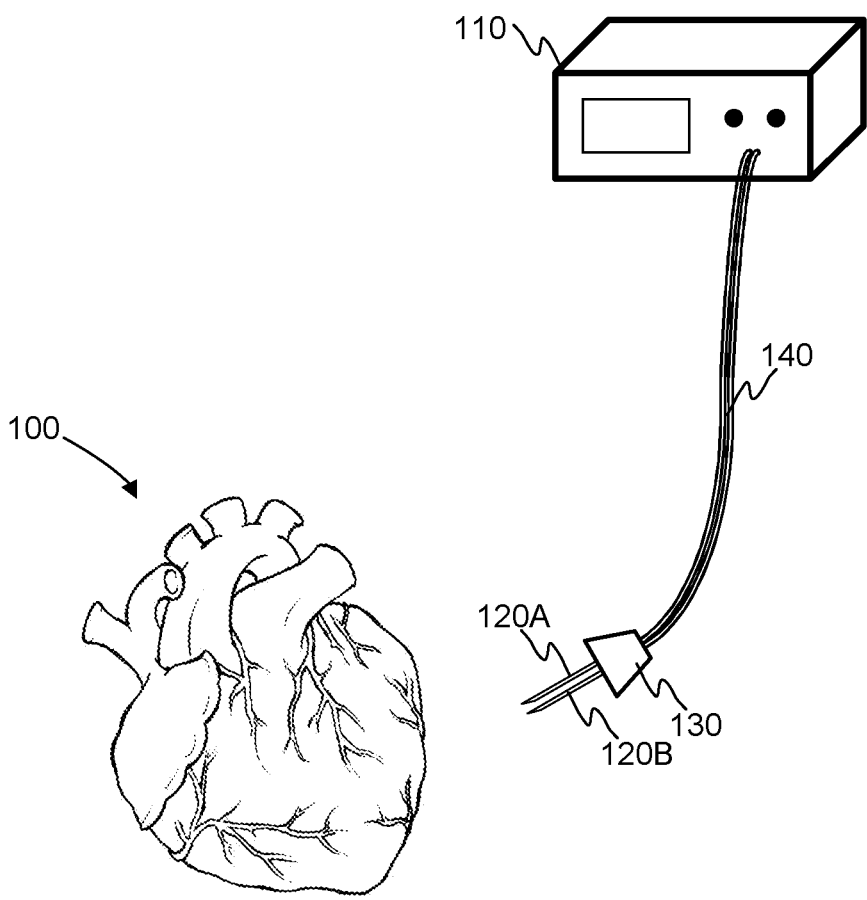

At least some aspects of the present technology are now described by referring to the embodiment of FIG. 1. There it is schematically illustrated a monitoring system for monitoring an object i.e. a tissue, such as a heart 100 muscle. An operation of the system is at least in part based on an optical spectroscopy by means of which it is possible to determine molecular concentrations and their oxygenation/oxidation ratios in a tissue under monitoring. Moreover, the system as schematically illustrated in FIG. 1 is applicable to monitor the tissue in question in real-time which also allows to derive conclusions on a development of a state of the tissue, and, thus, helps a planning of a treatment.

The monitoring system may comprise a control unit 110 for controlling an operation of the system. Moreover, the monitoring system may comprise at least two separate light guides 120A, 120B being distinct to each other at the end inserted to the tissue under monitoring.

A desired distinction between the light guides 120A, 120B at a measurement end may be arranged by delivering the light guides 120A, 120B through a jig 130 by means of which a distance between the light guides 120A, 120B may be fixed. Between the jig 130 and the control unit 110 the light guides 120A, 120B may travel together e.g. in a same lead 140 or distinct to each other. In accordance with an operation of the monitoring system the control unit 110 may be arranged to generate a light to a first light guide 120A for delivering the light to the tissue under monitoring, e.g. to the myocardium, whereas a second light guide 120B may be arranged to collect light from the tissue under monitoring, e.g. from the myocardium, and deliver it back to the control unit 110 for performing an analysis at least on a basis of the delivered and collected light. Still further, the system may comprise further elements and functionalities, such as an arrangement for providing cardiac pacing.

If a capability of providing cardiac pacing is integrated into the monitoring system, the control unit 110 may be provided with such a functionality and pacing leads may be brought in the same lead 140 as the light guides 120A, 120B, or at least along them, and the jig 130 may also be applied in bringing the pacing leads in the myocardium at least in part. Still further, the monitoring system, and especially the spectrometer probe, may comprise one or more arrangements and/or devices for attaching the measurement end of the probe to the tissue under monitoring as well as one or more arrangements and/or devices for improving a positioning of the light guides 120A, 120B in the tissue under monitoring as well as for improving a signal-to-noise ratio in the measurement.

Various aspects of the present technology will be discussed in the forthcoming description by non-limiting embodiments.

Figure 2:
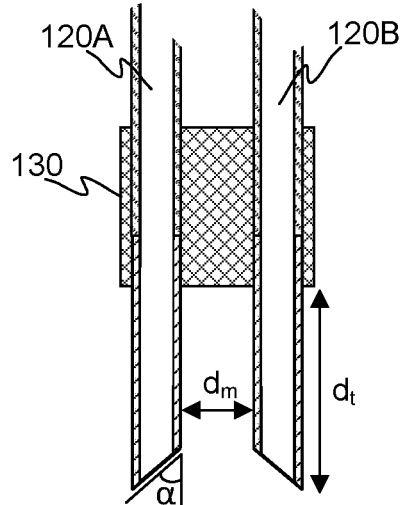
FIG. 2 illustrates schematically a first example of a myocardial spectrometer probe according to an embodiment of the invention.

FIG. 2 illustrates schematically, as a cross-sectional view, an example of a measurement end of a myocardial spectrometer probe according to an embodiment of the invention. A first light guide 120A and a second light guide 120B are arranged distinct to each other with a jig 130. A structure of the jig 130 is machined so that positions of the first and the second light guide 120A, 120B in the jig 130 define a mutual distance $d_m$ of the first and the second light guide 120A, 120B at the measurement end i.e. in the portion which is insertable in the tissue under monitoring.

In an embodiment, the mutual distance $d_m$ may be advantageously selected so that the second light guide 1208 is able to collect enough light to ensure adequate signal level for performing the monitoring but also so that at least portion of an intact tissue enters between the first and the second light guide 120A, 120B when the myocardial spectrometer probe is positioned in the tissue under monitoring.

In such an arrangement the light does not have any other way to enter the second light guide 120B from the first light guide 120A than through the tissue between the light guides 120A, 120B.

In one embodiment, a majority of the light emitted from the first light guide and received by the second light guide will have travelled through intact tissue, less than 10%, in particular less than 5%, preferably less than 1% of the light received by the second light guide will have travelled through any superficial tissue.

In one embodiment the mutual distance between the first light guide 120A and the second light guide 120B is between 0.1 mm and 5 mm, preferably between 1 mm and 2 mm. Moreover, the insertion depth $d_t$ of at least one of the light guides 120A, 120B is advantageously taken into account in the application area. In the context of the myocardial spectrometer probe, an applicable insertion depth $d_t$ may be about 3 mm-10 mm, preferably between 4 mm and 6 mm, which ensures that the light guide 120A, 120B reaches the myocardium through superficial layers to that, such as the epicardium, endocardium, epicardial fat, fibrous tissues, scarring, and similar, for measuring the molecular concentrations in the tissue. In one embodiment, at least one of the light guides 120A, 120B is at said insertion depth.

In one embodiment, a myocardial spectrometer probe comprises at least two separate light guides 120A, 120B, insertable into a tissue such that they are capable of reaching the myocardium through the superficial layers of the tissue, wherein a first light guide 120A, 120B is arranged to deliver light and a second light guide 120A, 120B is arranged to collect light, and wherein the first light guide 120A, 120B and the second light guide 120A, 120B are arranged distinct to each other at least in part.

In one embodiment, a myocardial spectrometer probe, comprises at least two separate light guides 120A, 120B, insertable in a tissue to an insertion depth of at least 3 mm, typically 3 to 10 mm, wherein a first light guide 120A, 120B is arranged to deliver light and a second light guide (120A, 120B) is arranged to collect light, and wherein the first light guide 120A, 120B and the second light guide 120A, 120B are arranged distinct to each other at least in part.

In some embodiments the light guides 120A, 120B may be coated in applicable manner. For example, the coating may be arranged so that in the portion of the light guides 120A, 120B entering the tissue the coating is arranged with a steel tubing providing protection and support to the light guides 120A, 120B.

Further, the portion of the light guides 120A, 120B heading out from the jig 130 towards the control unit 110 may be coated with applicable plastic material, such as with acrylic coating. Advantageously, the border between the different coating materials is arranged inside the jig 130 in order to maintain the coatings in place as well as to provide structural support in the joint location. The jig described here, provides the support to keep the light guides at predetermined distance relative to each other, can be any material or form which provides this function. The jig can be permanently fixed to the light guides or removable. Moreover, the coating of the light guides 120A, 120B especially on that side entering the tissue under monitoring may be selected so that it makes the light guides 120A, 120B stiff to support a penetration of a surface, and other layers, of the tissue in question.

In some embodiments the light guides (120A, 120B) may be made of biodegradable material.

In some embodiments the light guides may be inserted during or after manufacturing in a hole or holes in a solid block of material that protects the light guides during packaging, sterilization, shipping and storing. If the block of material has appropriate and known optical properties, it can also be used for pre-measurement calibration of the probe.

Moreover, as is derivable from FIG. 2, the tips of the light guides 120A, 120B may be designed in a manner a transfer of light between the light guides 120A, 120B is optimized. The designing of the tips may be performed by arranging an applicable angle α in the tip of the light guide 120A, 120B with respect to its longitudinal axis. In accordance with the present invention an advantageous angle α is 45°-90°, preferably 70°-90°. In addition to this, the tips of the first and the second light guides 120A, 120B may, at least in some embodiments, be arranged so that the openings of the light guides with the angle α (i.e. the angled surfaces) face each other as schematically illustrated in FIG. 2. The angle α may be generated in the light guides 120A, 120B e.g. by cleaving, by grinding or by polishing the light guide in question. Any material or lenses producing light converging, diverging or diffusion can be used in front of the light guide head or heads.

The first light guide 120A and the second light guide 120B may comprise one or more optical fibers (i.e. a single fiber or a fiber bundle) or implemented with a light tube. Independently of the physical implementation of the light guide the consideration about an applicable angle in the application area applies as discussed in the foregoing description.

A thickness of the light guide 120A, 120B, i.e. the entity selected to implement the role of the light guide 120A, 120B, is preferable between 100 μm and 400 μm.

Figure 3:
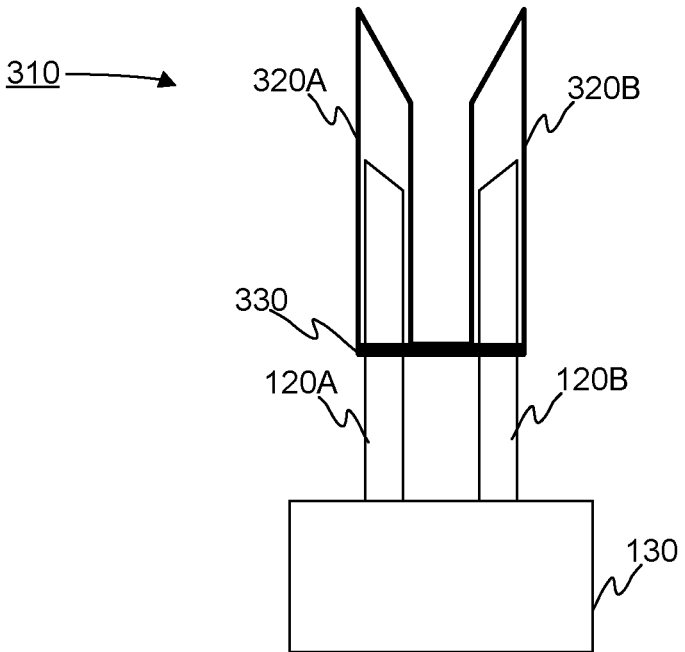
FIG. 3 illustrates schematically a second example of a myocardial spectrometer probe in a first state according to an embodiment of the invention.

FIG. 3 illustrates schematically some further aspects according to some embodiments of the invention. Namely, as mentioned above the tip of at least one light guide 120A, 120B shall be brought in the tissue whose characteristics is to be measured. For example, as regards to entering the myocardium the light guides 120A, 120B shall penetrate a plurality of layers being dense in nature before accessing the myocardium. In order to facilitate the penetration of the light guide 120A, 120B into the mentioned layer or layers, an insertion aid device 310 can be provided in the probe. The insertion aid device 310 is a device protecting the light guides 120A, 120B during an insertion of the probe into a measurement position, but also having a structure, and shape, enabling the penetration through the layers and, even, helping to maintain a mutual distance between the light guides 120A, 120B as designed. In accordance with an example embodiment the insertion aid device 310 comprises tubular members 320A, 320B into which the light guides are insertable. The tubular members 320A, 320B are preferably sharp at the end facing the tissue in order to cut the tissue for penetrating it. At the other end, the tubular members 320A, 320B are mounted on a support plane 330 facing e.g. the jig 310 at one state. As is derivable from FIG. 3 the size of the insertion aid 310, and especially the length of the tubular members 320A, 320B, is advantageously adjusted so that it does not disturb the delivery of light between the light guides 120A, 120B. In one embodiment, when the light guides 120A, 120B are inserted to a predetermined depth, they also extend out from insertion aid tubes such that the tubes to not interfere with the delivery of light between light guides 120A, 120B.

Figure 4:
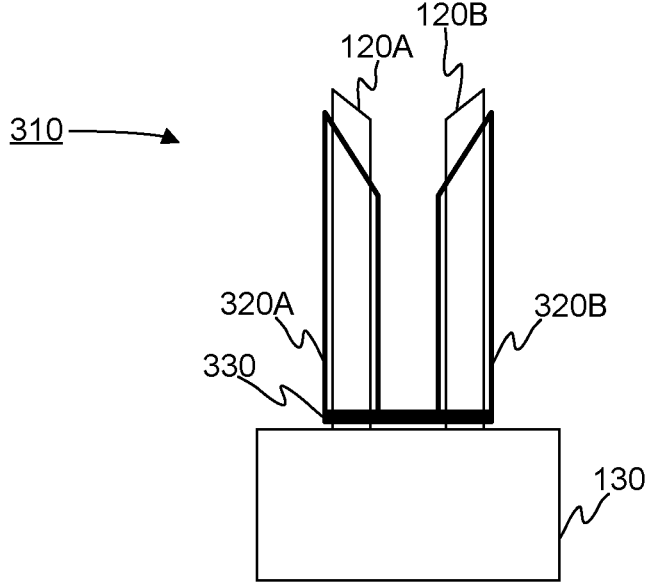
FIG. 4 illustrates schematically a myocardial spectrometer probe according to the second example in a second state according to an embodiment of the invention.

In accordance with some embodiments the insertion aid device 310 may be arranged to be movable at least in part with respect to the light guides 120A, 120B. Hence, a state shown in FIG. 3 may be considered to correspond to a situation in which the myocardial spectrometer probe is inserted into the tissue i.e. the insertion phase. In FIG. 4, on the other hand, it is schematically disclosed an example of the probe equipped with the insertion aid device 310 in a state that the probe has entered the tissue and 5 the light guides 120A, 120B are arranged out from the tubular members 320A, 320B. In other words, the state as illustrated in FIG. 4 is established when the probe is in a measurement position in the tissue. Hence, the insertion aid device 310 may be arranged slidably with respect to the light guides 120A, 120B e.g. in such a manner that in response to the tissue faces support plane 330 the insertion aid device 310 starts sliding along the light guides 120A, 120B e.g. until the support plane 330 reaches the jig 130. Naturally, at that state the light guides 120A, 120B slide out from the tubular members 320A, 320B in order to be used for the measurement.

The above described sliding mechanism may be achieved by adjusting the internal diameter of a tubular member 320A, 320B to the outer diameter of a respective light guide 120A, 120B so that the total friction between the entities exceeds the force required to penetrate the probe in the tissue. The friction may also be adjusted by modifying surfaces of the mentioned entities, such as by roughening the surfaces optimally. An applicable material of the insertion aid device 310 may e.g. be stainless steel (cf. e.g. hypodermic needle). Moreover, as mentioned, the ends of the tubular members 32A, 320B facing the tissue can be sharp, or at least their profile is preferably designed so that they ensure easy and safe insertion into the tissue.

Figure 5:
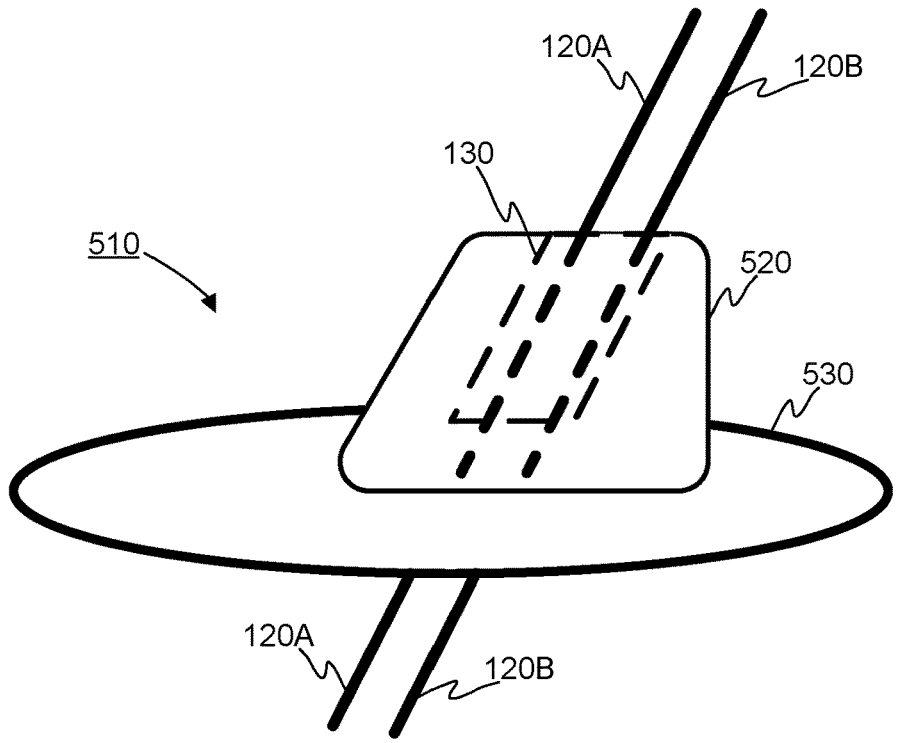
FIG. 5 illustrates schematically a third example of a myocardial spectrometer probe according to an embodiment of the invention.

FIG. 5 illustrates schematically aspects according to a further embodiment of the invention. In the embodiment a stopper device 510 is introduced in the myocardial spectrometer probe. The stopper device 510 provides a way to adjust at least the insertion depth of the light guides 120A, 120B into the tissue as desired within the application area. Moreover, the insertion angle may also be adjusted with the stopper device by arranging the light guides 120A, 120B to exit the stopper device 510 at a desired angle towards the tissue. Hence, by means of the stopper device 510 facilitates an adjustment of the position of the probe in the tissue, compared to a probe without the stopper device 510, as e.g. schematically illustrated in FIG. 2. The stopper device 510 may e.g. consist of a receiving section 520 and a light cover section 530. The receiving section 520 may e.g. comprise an adaptor for receiving a jig 130 holding the light guides 120A, 120B wherein by designing the adaptor in a desired angle it is possible to define at least in part an angle the light guides 120A, 120B enter to the tissue.

In other words, in one embodiment, a channel is arranged in the stopper device 510 to provide a path for the light guides 120A, 120B through the stopper device 510. Moreover, the light cover section 530 operates as a stopper against the tissue, but also prevents ambient light to enter the tips of the light guides 120A, 120B, and especially the light guide arranged to collect light. This may be important especially because the myocardial spectrometer probe may be used during cardiac operation wherein a good lightning is required. This provides a huge amount of ambient light, which reduces signal to noise ratio of optical measurement. Hence, the light cover portion 530 may be important to reduce noise during the measurement.

For example, an area of the light cover section may be 0.1 cm$^2$ to 5 cm$^2$, preferably 0.5 cm$^2$-2 cm$^2$. For example, the light cover section, and the whole stopper device 510, may be made of biodegradable material, polymer, metal, or glass. Furthermore, the light cover section 530 may be shaped so that it attaches to the tissue under monitoring well, or it may comprise one or more holes to be used for stitching the light cover section 530 to the tissue. Moreover, the light cover section 530 may be formed so that it may be removed easily, e.g. comprising an anchor for gripping, before a chest is closed when the open-heart surgery operation is completed, and the post-operative phase starts. Still further, in some embodiments the stopper device 510 may provide a counter force to the fixing device used for anchoring the probe in its measurement position as will be discussed in a forthcoming description. The stopper device 510 may be used together with the insertion aid device 310 similarly as described in the description of FIGS. 3 and 4.

Figure 6:
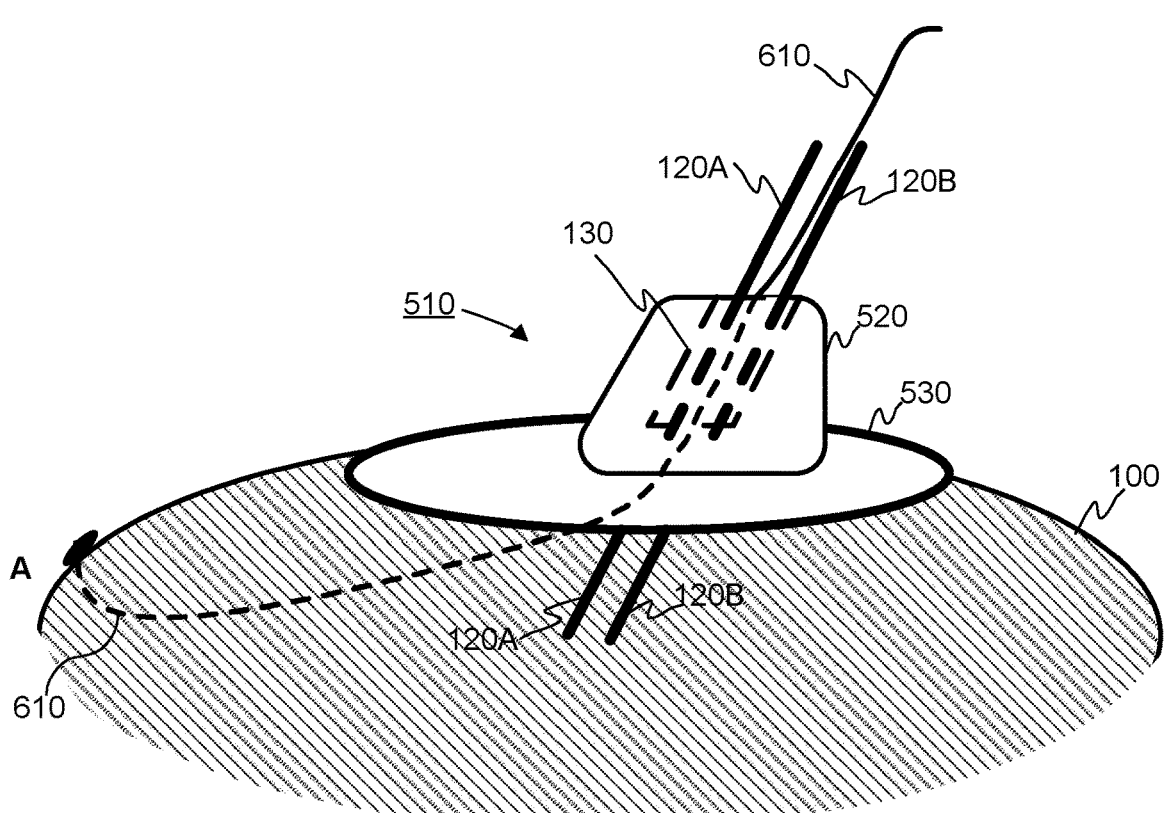
FIG. 6 illustrates schematically a fourth example of a myocardial spectrometer probe according to another embodiment of the invention.

FIG. 6 illustrates schematically a further example embodiment. In FIG. 6 the myocardial spectrometer probe is attached to an organ, which in the case shown in FIG. 6 is a heart. In the embodiment of FIG. 6 a fixing wire 610 is brought to myocardium along with the light guides 120A, 120B. The fixing wire 610 may be coupled to a jig 130 as well it may be arranged in the same channel as the light guides 120A, 120B traveling through a stopper device 510 in an embodiment the stopper device 510 is applied to. The fixing wire 610 may be fixed to a needle, and positioned, e.g. by using a needle in an open-heart surgery, so that it penetrates the tissue and is arranged to travel inside it a predetermined distance and exists the tissue at some location (indicated with letter 'A' in FIG. 6). The needle may be removed after positioning the fixing wire 610 to the tissue by cutting the wire in applicable position.

Advantageously, the end of the fixing wire 610 is fixed, preferable removably fixed, in an exit location. In such an arrangement the fixing wire 610 may be used in anchoring the myocardial spectrometer probe in the tissue in the monitoring. The anchoring may be achieved by tensioning the fixing wire 610 from the stopper device 510 end after the other end is fixed in the tissue at the exit location A. As a result, the probe itself attaches tightly against the tissue and light guides 120A, 120B remain stationary in a measurement position and artefacts caused by movement are, at least partially, eliminated. Anchoring of the fixing wires can be performed also with surgical clips, metallic or biodegradable.

In some embodiments, a pacing lead may be used as the fixing wire 610 as described. The pacing lead allows pacing of the heart muscle in any situation needed e.g. during a surgical operation and thereafter.

Figure 7A:
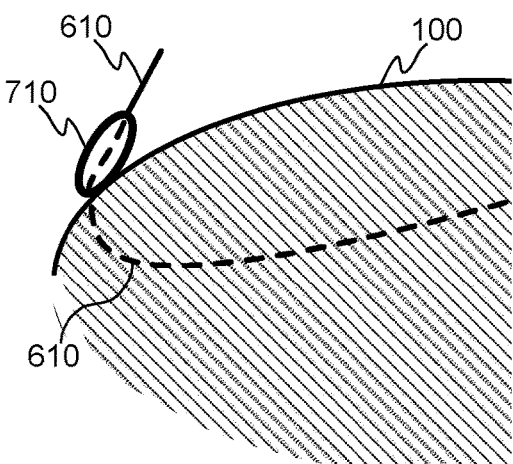
FIGS. 7A and 7B illustrate schematically further examples of myocardial spectrometer probes according to other embodiments of the invention, in particular of the embodiments of FIG. 6.
Figure 7B:
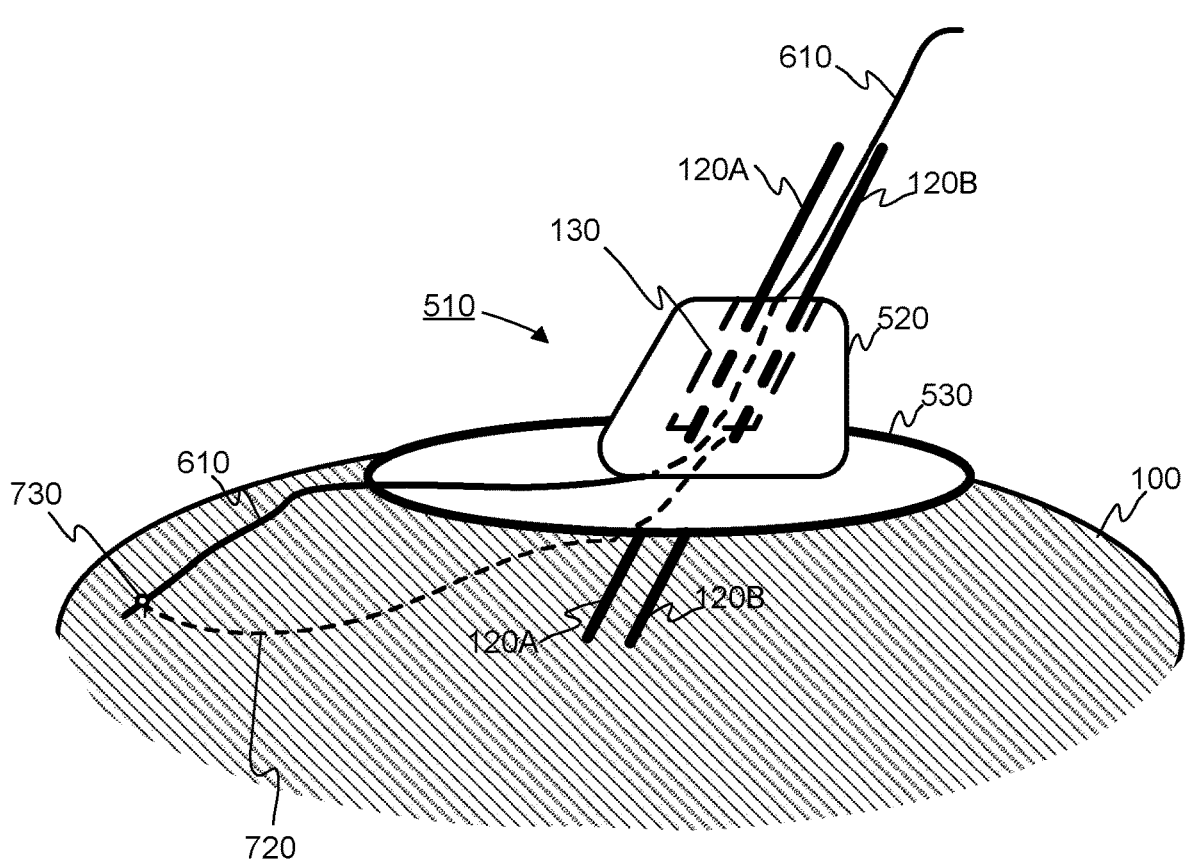

FIGS. 7A and 7B illustrate schematically some non-limiting examples of applicable solutions for fixing of the fixing wire 610, such as the pacing lead, into the tissue in question. For sake of clarity it is hereby assumed that the fixing wire 610 is a pacing lead. In FIG. 7A the example of the fixing is shown in an embodiment wherein the pacing lead is arranged to travel inside the myocardium (cf. FIG. 6). At the exit location an inflatable balloon device 710 is mounted to the end of the pacing lead exiting the tissue. The inflatable balloon device 710 is a ring-type device fixed around the pacing lead which provides the fixing the pacing lead at the exit location and, hence, enables the tensioning between the end of the pacing lead and the probe itself as described in the context of FIG. 6. The inflatable balloon device 710 may be mounted to the end of the pacing lead as non-inflated and it is inflated after that with an applicable inflating device. This may e.g. be done during an open-heart surgery. An advantage of the inflatable balloon device 710 is that after the open-heart surgery, when the probe and also the pacing lead, is left in the body, both the probe and the pacing lead may be removed remotely, i.e. percutaneously, outside the body by pulling the probe outwards after the balloon is remotely deflated. Deflation of the balloon device 710 allows for a pulling of the pacing lead back through the myocardium.

A fixing solution similar to the one schematically illustrated in FIG. 7A, in which the inflatable balloon device is applied, may be achieved with an anchor device made of material having a sufficient friction against a surface of the tissue and wherein the anchor device is positioned on the surface of the tissue. Now, the fixing wire is brought out from the tissue in the same manner as with the inflatable balloon device, but it is mounted to the anchor device in some manner.

For example, the anchor device may comprise a hole, or a slot, through which the fixing wire may be brought. The mutual dimensioning of the hole or the slot and a diameter of the fixing wire is advantageously selected so that their mutual friction is sufficient to enable tensioning of the probe by pulling the fixing wire outwards from the tissue at the probe end. However, in a preferred solution the friction between the entities is arranged so that with a pulling exceeding a selected level the fixing wire starts sliding though the hole, or the slot, and in than manner the fixing wire may be removed from the tissue. For example, the anchor device may be made of plastics or any other material applicable to operate in the described manner. A clamp may also be applied to. In some embodiments the anchor device may be made of biodegradable material enabling leaving the anchor device inside the body.

FIG. 7B depicts schematically another example of fixing the pacing lead in the heart according to another embodiment of the invention. Here, the pacing lead is arranged to travel on the myocardium i.e. it does not go through a light cover section 530 but is arranged to travel on it. Additionally, a wire 720 is arranged to travel inside the tissue providing a fixing arrangement 730, such as a loop, in a position in which the wire 720 exits the tissue. By guiding the pacing lead (cf. 610 in FIG. 7B) through the loop and tensioning the wire from the probe end, the pacing lead may be fixed on the tissue by anchoring it accordingly. This kind of fixing may be arranged during an open-heart surgery. The fixing according to the example of FIG. 7B also allows a remote removal by loosening the wire 720 and pulling the pacing lead out. After that also the wire may be removed. In some embodiments of the invention the fixing of the pacing lead may be performed with the fixing mechanism of FIG. 7B so that a hole is arranged in the light cover section 530 through which the wire and the loop is arranged on the surface of the light cover section 530. By guiding the pacing lead through the loop the tensioning may be arranged against the surface of the light cover section 530 minimizing damages to the tissue in question due to tensioning. In some further embodiments the damages to the tissue may be avoided in the embodiment of FIG. 7B by arranging a screen plate, made e.g. from biodegradable material, under the pacing lead at the position in which the wire 720 exits the tissue.

Moreover, the arrangement schematically illustrated in FIG. 7B may also be arranged vice versa so that wire 720 of FIG. 7B is implemented with the pacing lead having a loop at the end of the lead and a wire is arranged to travel on the myocardium in a similar way as the pacing lead in FIG. 7B. Now, by inserting the wire traveling on the myocardium through the loop arranged at the end of the pacing lead, the fixing may be arranged by pulling the pacing lead traveling inside the myocardium.

In order to enhance a removal of the pacing leads, but also the light guides 120A, 120B from the body, they may be enclosed either separately or together in some combination within a plastic or a silicone tube. The diameter of the tube can be adapted to the diameter of the jig 120 holding the light guides 120A, 120B, thus enabling smooth removal of the removable parts of the probe. The pacing leads themselves may be made of biocompatible material, such as stainless steel. For example, the pacing leads may be 0.1 m-10 m long depending on a need.

Still further, in some embodiments the light cover portion 530 may be arranged to operate as an anode or a cathode for a bipolar pacing implementation in accordance with a role of the end of the pacing lead (i.e. in a role of the other electrode). In such an embodiment at least a portion of the light cover portion 530 is made of conductive material into which another pacing lead is connected to. Correspondingly, in some further embodiments an insertion aid device 310 may be used as an electrode for the pacing implementation. Dependent on the implementation for example one of the tubular members 320A, 320B may be connected to one of the pacing leads and advantageously insulated from other portions of the insertion aid device 310 in order to establish the electrode with the other electrode established at the end of the pacing lead. Still further, in case the light guides 120A, 120B are coated with a steel tubing the pacing leads may be connected to at least one steel tubing and in that manner to establish an electrode.

Regarding a removal of the myocardial spectrometer probe a further note maybe given with respect to light cover section 530. In some embodiments the light cover section 530, at least in part due to its shape, may be left on the heart after the removal of the probe. In such an implementation the light cover section 530 and a receiving section 520 of the probe may be removably coupled to each other. The coupling may be arranged so that the de-coupling requires less power than the removal of the light cover section 530 from the tissue into which it is mounted to. Hence, as a result of pulling the probe outwards the receiving section 520 and the light cover section 530 are decoupled from each other leaving the light cover section 530 on a surface of the tissue in question. In such an implementation the light cover section 530 is advantageously made of biodegradable material, such as an applicable polymer.

In another embodiment the light cover portion 530 may be made of foldable material at least in part. Now, when the probe is to be removed from the tissue and pulled outwards from the body, the foldable light cover portion 530 shapes so that the light cover portion 530 may enter in a folded shape through a hole along which the probe is removed from the body.

Still further, in some embodiments the light cover section 530 of the probe may be attached with the tissue by suturing it with a number of sutures to the tissue. In such an embodiment the light cover section 530 may comprise one or more holes to be used for attachment e.g. with sutures. Advantageously, the sutures release the light cover section 530 from the tissue in response to a pulling power exceeding a predetermined value. The sutures may be made of biodegradable material, or even from stainless steel or other biocompatible material. In some embodiments the suture made of conductive material may be used as an electrode for cardiac pacing wherein a pacing lead is coupled to such a suture.

Figure 8:
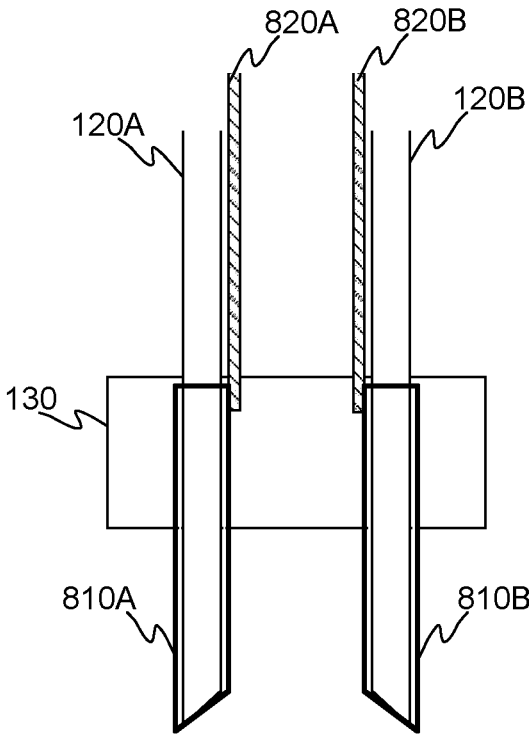
FIG. 8 illustrates schematically a further example of a myocardial spectrometer probe according to an embodiment of the invention.

FIG. 8 illustrates schematically a further exemplifying embodiment of a probe according to the present invention. The exemplifying embodiment is based on an implementation in which at least some portions of an insertion aid device is integrated with a jig 130. In the embodiment the tubular members are implemented as electrically conductive tubes 810A, 8108, such as metallic tubes, which are fixed in the jig 130 in an applicable manner, such as by gluing them thereto. The electrically conductive tubes 810A, 810B, as the tubular members, provide a path for respective light guides 120A, 120B to enter the tissue under monitoring. In other words, the electrically conductive tubes 810A, 8108 provide a channel through the jig 130 for positioning the light guides 120A, 120B appropriately for monitoring. The electrically conductive tubes 810A, 810B of the embodiment as disclosed in FIG. 8 may be implemented with an applicable coating of the light guides 120A, 1206 as described in the foregoing description. In accordance with the example embodiment a respective pacing lead 820A, 820B is arranged for each electrically conductive tube 810A, 810B so as to establish an anode and a cathode for providing bipolar pacing to the heart muscle if needed. The pacing lead 820A, 820B and the respective electrically conductive tube 810A, 810B are, hence, in electrical contact with each other to conduct electricity over the contact. The contact point may be arranged so that it is inside the jig 130 and, for example, so that an applicable connector is arranged to form the contact into which the pacing lead 820A, 820B may be inserted. Alternatively, or in addition, the contact may be implemented by welding, soldering or pressing. Additionally, the jig 130 is made of electrically non-conductive material. The light protection cover may also be used with the example embodiment as depicted in FIG. 8. The fundamental idea of FIG. 8 may also be applied in the context of a separate insertion aid (cf. e.g. embodiment of FIG. 3 and FIG. 4) by arranging the pacing leads 820A, 820B to the respective tubular members 320A, 320B, wherein the tubular members 320A, 320B are separated from each other with electrically non-conductive material (cf. e.g. a material of the support plane 330).

Moreover, in some exemplifying embodiments the myocardial spectrometer problem may further comprise a removably mountable protection cover to protect the first light guide 120A, 120B and the second light guide 120A, 120B e.g. during a non-use of the probe, such as during storing and shipping the probe. In some further embodiments the protection cover is implemented so that it may operate as a calibration target for calibrating a measurement system applying the myocardial spectrometer probe. In order to enable calibration characteristics of the protection cover shall be selected accordingly. In an example embodiment the material of the protection cover may be selected so that an absorption coefficient for light within a wavelength 600-900 nm used in the measurement shall be constant and reasonable low, such as below 0.001 mm$^{-1}$.

Additionally, in one embodiment, the scattering coefficient of the material corresponds to the reduced scattering coefficient of the tissue under monitoring, such as ~1 mm$^{-1}$.

Additionally, the size and the shape of the protection cover is preferably designed so that border regions of the material, and cavities into which the light guides are inserted, do not cause disturbance due to background light to the calibration. For example, the shape may be such that it extends at least 3 mm in every direction from the tips of the light guides 120A, 120B. An applicable material may e.g. be clear epoxy resin and titan dioxide or optical PTFE.

Even if the foregoing description is provided in such an environment that the first and the second light guide 120A, 120B reach the same depth inside the tissue the present invention is not only limited to such an implementation. Namely, the insertion depth between the light guides 120A, 120B may vary as long as the collected light enables a meaningful measurement result with respect to monitored parameters. In some embodiment of the invention the other light guide 120A, 1208 may be positioned on the surface of the tissue, or so that the insertion depth is such that an epicardium is only penetrated whereas the other light guide 120A, 120B is taken deeper in the tissue.

Generally speaking, the myocardial spectrometer probe may be applied in monitoring molecular concentrations in the tissue in real-time e.g. during and after an open-heart surgery. An applied spectroscopy may be so-called diffuse optical spectroscopy, diffuse reflection spectroscopy, Raman spectroscopy, Fourier-transform spectroscopy or fluorescence spectroscopy, for example.

Thus, a method of monitoring molecular concentrations in a tissue of interest by spectroscopy, comprises providing at least two separate light guides, a first light guide being arranged to deliver light and a second light guide being arranged to collect light. The light guides are inserted into the tissue of interest, in particular heart muscle, such that at least a portion of intact tissue separates the first light guide from the second light guide. Thus, light delivered by the first light guide will travel through said intact tissue to reach the second light guide.

Further, in the method light is delivered (or emitted) from the first light guide and light delivered from the first light guide is received by the second light guide. There is a plurality of light pulses delivered and received to form a plurality of signals corresponding to the light collected. The signals thus obtained are used for monitoring the tissue of interest. Typically, 1 to 100 pulses, in particular 2 to 50 pulses, such as 5 to 20 pulses, or 8 to 15 pulses, are emitted and received per second.

In an embodiment the measurement system as disclosed in FIG. 1, or in a context of any of the embodiments as described herein, produces clinically relevant information of heart metabolism measured simultaneously from intracellular organisms, within cytosol, extracellular molecular concentrations and intravascular concentrations. In another embodiment the system may measure molecular concentrations within the oxidative phosphorylation chain within mitochondria during cardiac surgery.

In an embodiment, the myocardial spectrometer probe is used in a method of monitoring variations in concentrations of enzymes, responding to mitochondrial stress.

In an embodiment, the myocardial spectrometer probe is used for monitoring molecular concentrations of catalase, superoxide dismutase and peroxidases and combinations thereof.

Moreover, the myocardial spectrometer probe may be connected to an online monitor, e.g. implemented to the control unit, showing in real-time relevant information regarding the myocardial metabolism to the medical personnel and, thus, enabling to react accordingly in the situation.

As is derivable from the foregoing description at least some essential characteristics of the present invention are that the light guides 120A, 120B, among which at least one first brings in the light and at least one second collects the light, are arranged distinctly to each other in the measurement position in the tissue under monitoring, such as a myocardium, in order to establish a reliable measurement setup. in which at least part of the emitted light transfers through the tissue between the light guides 120A, 120B. The distance between the light emitting light guide 120A, 120B and the light collecting light guide 120A, 120B is predefined.

Depending on the measurement type, i.e. if it is performed with a beating heart or with a resting heart, the fixing of the light guides 120A, 1208 to the tissue may be required.

The invention as such also allows that in a context of an open-heart surgery temporary pacing wires may be used to support the patient after the surgery. The distinct positioning of the light guides also provides a possibility to combine temporary cardiac pacing wires in the same construction in the manner as described for example by covering the light guides by metal, or any other conductive material. Still further, the construction as described enables an implementation of further measurements from the tissue, such as temperature measurement of the tissue with electric or optical means. In other words, an applicable sensor may be implemented in the probe to a portion, such as the light guide or the insertion aid device, penetrating the tissue from which the measurement data may be obtained. Alternatively, or in addition, the temperature may be determined from the measurement data obtained with the light guides i.e. optically.

The specific examples provided in the description given above should not be construed as limiting the applicability and/or the interpretation of the appended claims. Lists and groups of examples provided in the description given above are not exhaustive unless otherwise explicitly stated.

What is claimed is:

1. A myocardial spectrometer probe, comprising:
   at least two separate light guides, insertable in a tissue, wherein a first light guide is arranged to deliver light and a second light guide is arranged to collect light, and wherein the first light guide and the second light guide are arranged distinct to each other at least in part,
   wherein a tip of the first and second light guide are angled in 70-90 degrees with respect to a respective longitudinal axis of the first and second light guide,
   wherein the light guides are coated so as to make the light guides stiff to support penetration of a surface, and other layers, of the tissue in question, and
   wherein the first light guide and the second light guide are arranged distinct to each other by mounting the first and second light guides in a jig so that at least a portion of intact tissue separates the first light guide from the second light guide once they are inserted to the tissue.

2. The myocardia spectrometer probe of claim 1, wherein the first and second light guides are capable of reaching the myocardium through the superficial layers of the tissue.

3. The myocardial spectrometer probe of claim 1, wherein the first light guide and the second light guide are implemented with one of: as a single optical fiber, optical fiber bundles, or a light tube.

4. The myocardial spectrometer probe of claim 1, wherein at least a portion of at least one of the first or second light guides insertable to the tissue is coated with a steel tubing.

5. The myocardial spectrometer probe of claim 4, the myocardial spectrometer probe further comprising one or more pacing leads arranged to travel along at least one of the first or second light guides.

6. The myocardial spectrometer probe of claim 5, wherein at least one of the pacing leads is electrically connected to the steel tubing coated on the at least portion of the at least one of the first or second light guides.

7. The myocardial spectrometer probe of claim 6, wherein a first pacing lead is electrically connected to the steel tubing of the first light guide and a second pacing lead is electrically connected to the steel tubing of the second light guide so as to form a bipolar pacing arrangement comprising an anode and a cathode.

8. The myocardial spectrometer probe of claim 1, wherein the myocardial spectrometer probe further comprises a stopper device for adjusting at least one of: an insertion depth of at least one of the first or second light guides in the tissue or an insertion angle of at least one of the first or second light guides in the tissue.

9. The myocardial spectrometer probe of claim 8, wherein the stopper device comprises a receiving section for receiving at least the first and second light guides and further comprises a light cover section for preventing ambient light to enter the tissue, at least in part.

10. The myocardial spectrometer probe of claim 9, wherein the receiving section and the light cover section of the stopper device are mounted together removably.

11. The myocardial spectrometer probe of claim 9, wherein a fixing wire is arranged to travel through the stopper device, an end of the fixing wire is arranged to be fixed to the tissue for enabling a tensioning of the first and second light guides with a fixing location of the fixing wire.

12. The myocardial spectrometer probe of claim 11, wherein the fixing wire is a pacing lead.

13. The myocardial spectrometer probe of claim 11, wherein the fixing wire is arranged with one of: an inflatable balloon device, a fixing arrangement arranged with a second wire forming an anchor for the fixing wire, an anchor device.

14. The myocardial spectrometer probe of claim 1, wherein the myocardial spectrometer probe further comprises an insertion aid device for penetrating a surface of the tissue and for inserting the first and second light guides in the tissue, wherein the insertion aid device comprises at least one tubular member inside which the first and second light guide are arranged.

15. The myocardial spectrometer probe of claim 14, wherein the at least one tubular member is arranged slidably with respect to the first and second light guide.

16. The myocardial spectrometer probe of claim 14, wherein the insertion aid device is arranged to operate as an electrode for a pacing lead coupled to the insertion aid device.

17. The myocardial spectrometer probe of any one of claim 14, wherein an end of the at least one tubular member of the insertion aid device arranged for facing the tissue is sharp in shape, and wherein the insertion aid device comprises stainless steel, a ceramic material, a composite material, or a combination thereof.

18. The myocardial spectrometer probe of claim 1, wherein at least a portion of the myocardial spectrometer probe is made of biodegradable material.

19. The myocardial spectrometer probe of claim 1, wherein the myocardial spectrometer probe further comprises means for providing measurement data representing a temperature of the tissue.

20. The myocardial spectrometer probe of claim 1, wherein the myocardial spectrometer probe further comprising a removably mountable protection cover to protect the first light guide and the second light guide, and wherein the protection cover is arranged to operate as a calibration target for calibrating a measurement system applying the myocardial spectrometer probe.

21. The myocardial spectrometer probe of claim 1, wherein the first light guide and the second light guide are insertable into the myocardium tissue between the epicardium and endocardium, such that light delivered by the first light guide will travel through intact tissue in the myocardium to reach the second light guide.

22. The myocardial spectrometer probe of claim 1, wherein the myocardial spectrometer probe is configured for monitoring molecular concentrations in tissue in real-time.

23. The myocardial spectrometer probe of claim 22, wherein the monitoring comprises diffuse optical spectroscopy, Raman spectroscopy, Fourier-transform spectroscopy, or fluorescence spectroscopy.

24. A method of monitoring molecular concentrations in a tissue of interest by spectroscopy, comprising:

providing at least two separate light guides, insertable into the tissue, wherein a first light guide is arranged to deliver light and a second light guide is arranged to collect light, inserting the light guides into the tissue of interest such that the first light guide and the second light guide are arranged distinct to each other by mounting the first and second light guides in a jig so that at least a portion of intact tissue separates the first light guide from the second light guide, so that light delivered by the first light guide will travel through said intact tissue to reach the second light guide, repeatedly delivering light from the first light guide and collecting light delivered from the first light guide by the second light guide, to form a plurality of signals corresponding to the light collected; and monitoring the plurality of signals thus obtained wherein a tip of the first and second light guide are angled in 70-90 degrees with respect to a respective longitudinal axis of the first and second light guide, and wherein the light guides are coated so as to make the light guides stiff to support penetration of a surface, and other layers, of the tissue in question.

25. The method of claim 24, further comprising at least one of:

monitoring variations in concentrations of enzymes, responding to mitochondrial stress; or monitoring molecular concentrations of catalase, superoxide dismutase, peroxidases, or combinations thereof.

\* \* \* \* \*